United States Patent [19]

Ross, Jr. et al.

[11] 4,049,382

[45] Sept. 20, 1977

[54] TOTAL RESIDUAL CHLORINE

[75] Inventors: James W. Ross, Jr., Hull; Albert A. Diggens, Newton, both of Mass.

[73] Assignee: Orion Research Incorporated, Cambridge, Mass.

[21] Appl. No.: 768,953

[22] Filed: Feb. 16, 1977

[51] Int. Cl.² .................... G01N 33/18; G01N 27/52
[52] U.S. Cl. .............................. 23/230 R; 23/253 R; 204/1 T
[58] Field of Search .................. 23/230 R, 253 R; 204/1 T

[56] References Cited
U.S. PATENT DOCUMENTS

| 3,413,199 | 11/1968 | Morrow, Jr. ............... | 23/230 R X |
| 3,937,613 | 2/1976 | Rosicky ..................... | 23/230 R |

OTHER PUBLICATIONS

Hallinan, "Test for Residual Chlorine," Indus. & Eng. Chem. (Anal. Edit.), vol. 12, 1940, pp. 452-453.

Primary Examiner—R.E. Serwin

[57] ABSTRACT

A method of monitoring the total residual chlorine in solution. A sample stream is extracted from the solution and mixed with a reagent stream containing a dissociated complex of alkali metal ion and iodide ion, and an excess amount of iodide ion. Iodide ion reacts with all the residual chlorine in the sample stream and is converted to iodine. The activity of iodine is then measured in the resultant mixed stream with a first and second electrochemical potentiometric electrode, the first electrode having a noble metal oxidation-reduction element, and the second having an iodide sensitive membrane element. The total residual chlorine is determined from the activity of the iodine.

9 Claims, 2 Drawing Figures

TOTAL RESIDUAL CHLORINE

BACKGROUND OF THE INVENTION

1. Field of Invention

This invention relates to potentiometric measurements.

2. Prior Art

The removal of cyanides and other effluents from waste water, the cleansing of canned vegetables and poultry, and the purity of water used for industrial cooling and public consumption all depend on the use of chlorine additives, making the measurement of total residual chlorine of special interest. The measurement of residual chlorine is usually performed by colorimetry, ASTM D 1235-68; by amperometric titration, ASTM D 1253-76, D 1427; or by starch iodide titration, ASTM D 1253-76, D 1427.

Quick testing is a limiting requirement common to each of these three methods, and indeed, to any measurement of total residual chlorine. ASTM recommends that all tests be completed within 5 minutes of sampling, since chlorine demand of the sample may quickly diminish the residual chlorine present, resulting in determinations that are too low.

The colorimetric method measures total residual chlorine by reacting a sample, under acid conditions, with orthotolidine to form the yellow holoquinone of orthotolidine dihydrochloride. The color developed is approximately proportional to the amount of chlorine residual present and is quantitatively evaluated by comparison with standard colors.

The amperometric titration method prescribes a procedure for electrochemically determining the point at which a reducing agent reacts with all the total residual chlorine to eliminate all current. Total residual chlorine is calculated from the amount of reducing agent added to the sample. The titration endpoint is graphically determined on a plot of measured current versus volume of reducing agent.

The third method of measurement is starch iodide titration. This method involves the addition of iodide to the sample, reacting with all the total residual chlorine to form iodine, which in turn is reduced by titration with phenylarsene oxide solution. The iodine concentration is calculable from the volume of reagent added. The total residual chlorine concentration is then calculated from the relationship between iodine concentration and original total residual chlorine.

The starch iodide method includes any iodine present in the sample prior to the addition of iodide, introducing errors in total residual chlorine measurement. The inclusion of iodine present before testing for chlorine is of practical significance, however, since both chlorine and iodine are oxidizing halogens frequently monitored in waste water.

The colorimetric method is ineffective in both colored and dirty water, yielding results with poor precision and accuracy, thus placing a severe limitation on its widespread use. Several other limitations arise in the use of the amperometric and starch iodide titration methods. Since both require accurate measurement of volumes and precise use of laboratory equipment in a short time span, trained technicians are necessary for accurate results. In the amperometric method, the titration endpoint is interpreted from the current — volume curve, again calling for special expertise in performing the test in a repeatable fashion. There is also the inconvenience of a time delay, since data manipulation precedes the test results.

SUMMARY OF THE INVENTION

The present invention contemplates an improved method of determining total residual chlorine. The primary object of the invention is to provide a method of determining total residual chlorine in a time period wherein errors due to chlorine demand of the sample will be minimized. Another object of the invention is to measure total residual chlorine in dirty or colored water with precision and accuracy.

A further object is to measure total residual chlorine without trained technical personnel by a method reducing the opportunity for errors in procedure, measurement, and data interpretation.

Yet another object of the invention is to provide a method of measuring the activity of iodine in solution.

The objects of the present invention are effected by mixing continuously with a sample stream of the test solution, a reagent comprising a dissociated complex of alkali metal ion and iodide ion not present in the solution, and an excess amount of iodide ion. Iodide ion reacts with all the residual chlorine in the sample stream and is converted to iodine. The activity of iodine is then measured in the resultant mixed stream with a first and second electrochemical potentiometric electrode, the first electrode having a noble metal oxidation-reduction element, and the second having an iodide sensitive membrane element. The total residual chlorine is determined from the activity of the iodine.

Other objects, aspects and advantages will in part be obvious and will in part appear hereinafter. The invention comprises the method exemplified in the following detailed disclosure, and the scope of the application of which will be indicated in the claims.

BRIEF DESCRIPTION OF THE DRAWINGS

For a more full understanding of the nature and objects of the present invention, reference should be made to the following detailed description taken in connection with the accompanying drawings wherein.

PREFERRED EMBODIMENT

Figure 1:
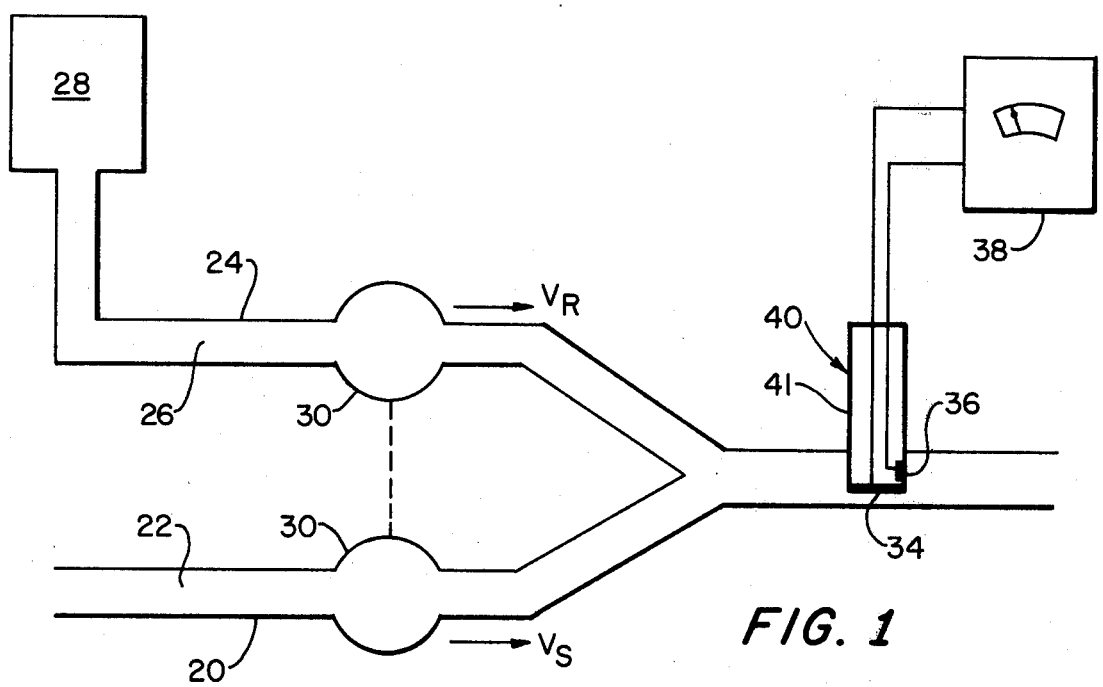
FIG. 1 shows a schematic diagram of a preferred form of the present invention.

Referring now to the drawings there is shown in FIG. 1 a first conduit 20 for conveying a sample stream of fluid 22 which is being monitored for the presence of total residual chlorine, and a second conduit 24 which is intended to convey a stream of reagent fluid 26 containing a reagent comprised of a dissociated complex of alkali metal ion and iodide ion, and an excess of iodide ion. Reagent 26 is supplied from reservoir 28. The supply of sample fluid 22 is not shown but obviously can be obtained from the source to be monitored for total residual chlorine, such as the coolant from an industrial waste water plant.

The device includes pump means 30, in its preferred form, shown as a dual pump, which is utilized to deliver an output of reagent and sample streams at pumped flow rates indicated respectively as $V_r$ and $V_s$. The dual pump ensures that minor variations in flow due to small pumping deviations do not alter the relative rates of reagent and sample addition. Pump means 30 are disposed to pump the liquids in conduits 20 and 24 into a common conduit 32, wherein reagent stream 26 and sample stream 22 are intimately mixed.

Immersed in the intimate mixture of reagent and sample streams is residual chlorine system electrode 40, combining in a single structure two Nernstian electrodes, 34 and 36, the former being an oxidation-reduction element composed of a noble metal, typically platinum, the latter having a solid, substantially imporous membrane sensitive to iodide ions.

The electrode, 40 comprises an elongated, hollow tube, or container 41, open at one end. The container typically is formed of a liquid-impervious, substantially rigid, electrically-insulating material, such as unplasticized polyvinylchloride, polytetrafluoroethylene, glass or the like, substantially inert to solutions being tested and with which the container might be placed in contact.

Mounted in the open end of container 41 and sealing said open end, is oxidation-reduction element 34, composed of a noble metal, typically platinum.

Mounted in an aperture in the wall of container 41 and sealing said aperture, is reference element 36, sensitive to iodide ions and comprising a solid, substantially imporous membrane having a surface layer thereof adapted to contact said solution, said surface layer comprising an intimate mixture of $Ag_2S$ with $AgI$.

Oxidation reduction element 34 and reference element 36 are connected electrically to electrometric device 38, so that the potential difference between said elements can be measured.

Electrode 40 is immersed in the mixture of sample stream and reagent stream so that both oxidation-reduction element 34 and reference element 36 are completely submerged in said mixture, each element in contact with said mixture.

Reference element 36 need not be incorporated in the same structure as oxidation-reduction element 34. Reference element 36 may form a separate structure but must contact the mixture of reagent and sample streams and must be connected electrically to electrometric device 38.

The following is the equation for the reaction of free chlorine, $Cl_2$, one form of residual chlorine, with iodide ion to form iodine.

$$Cl_2 + 2I^-_{100} = I_2 + 2Cl^- \qquad (1)$$

As equation (1) shows, iodine is formed in one-to-one correspondence with the residual chlorine lost in the sample. Other forms of residual chlorine will similarly react with iodide to form iodine in one-to-one correspondence with residual chlorine lost. Iodine is measured with electrode 40.

The Nernst equation describes the electric potential developed by each element. For the platinum oxidation-reduction element 34:

$$E_1 = E'_1 + (RT/2F) \log [(I_2)/I^-)^2] = E'_1 + (RT/2F) \log (I_2) - (RT/2F) \log (I^-)^2 \qquad (2)$$

For the iodide sensitive element 36:

$$E_2 = E'_2 - (RT/F) \log (I^-) = E'_2 - (RT/2F) \log (I^-)^2 \qquad (3)$$

Subtracting equation (3) from (2):

$$E_3 = E_1 - E_2 = E'_3 + \log (RT/2F) (I_2) \qquad (4)$$

Equation (4) indicates that the potential difference $E_3$, between the two elements is proportional to the concentration of iodine, and therefore, from equation (1), proportional to the concentration of total residual chlorine. By measuring the electric potential difference between oxidation-reduction element 34 and reference element 36, the iodine concentration may be determined. As equation (1) illustrates, the iodine concentration provides a direct measurement of the amount of total residual chlorine reduced to chloride ion by the addition of iodide.

If iodine is present in the sample prior to the addition of iodide, the amount of iodine produced by the reaction with residual chlorine is not shown by total iodine content. The correction could be made by measuring iodine content in the sample stream prior to the addition of iodide or by removing iodine prior to the reaction. Neither of these correction methods are of practical use, however, since both chlorine and iodine are oxidizing halogens frequently monitored in waste water and their combination in one measurement is a practical advantage. The use of sea water for chlorination is the only significant situation where iodine is present in appreciable quantities and separation from total residual chlorine is desirable. In such a situation, correction for the presence of iodine can be made by measuring the concentration with electrode 40 in sample stream 22 prior to the addition of reagent stream 26.

A number of aqueous solutions were mixed with different precisely serially diluted concentrations of total residual chlorine. The iodide reagent was buffered to an optimal pH by the addition of an acid reagent. A value of about 4.5 was chosen as optimum because at this slightly acedic pH, chlorine and chloramines react rapidly with iodide to form iodine while other oxidizing species such as Cr(VI) and Fe (III) do not.

Figure 2:
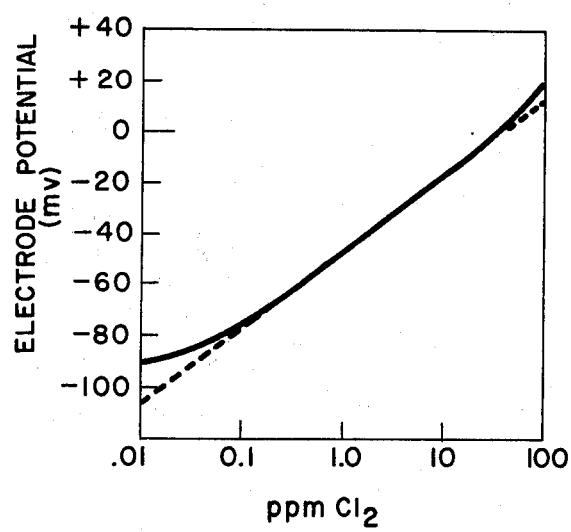
FIG. 2 is a semi-logarithmic graph showing the response of the system for total residual chlorine measurement to solutions of different residual chlorine activities.

An electric potential is developed between the oxidation-reduction element 34 and the reference element 36. FIG. 2 shows typical changes in the electric potential with changes in chlorine concentration. The abscissa is logarithmic, showing chlorine concentration in parts per million. The ordinate is linear, showing millvolts of electrode potential in intervals of twenty. The curve shows a Nernstian response by the residual chlorine electrode in the range from 15 to 70 ppm $Cl_2$ and an approximately Nernstian response up to 100 ppm and down to 0.01 ppm. Higher concentrations of total residual chlorine can also be measured by dilution of the sample stream prior to testing. Readings were taken immediately upon insertion of the electrode in the sample-reagent mixture.

As shown above, total residual chlorine concentration is determined by reacting iodide with the chlorine to form iodine and measuring the concentration of iodine thereby produced. Equation (1) shows the relationship between free chlorine consumed and iodine produced. The same measuring technique may be used to determine the concentrations of other species, such as ozone ($O_3$), bromine ($Br_2$), and cupric ion ($Cu^{+2}$), as equations (5), (6) and (7) show.

For ozone ($O_3$):

$$6H^+ + O_3 + 6I^-_{100\%} 3I_2 + 3H_2O \qquad (5)$$

For bromine ($Br_2$):

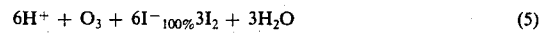

$$Br_2 + 2I^- \xrightarrow{100\%} I_2 + 2Br^- \quad (6)$$

For cupric ion ($Cu^{+2}$):

$$Cu^{+2} + 2I^- \xrightarrow{100\%} I_2 + Cu \quad (7)$$

In each of equations (5), (6), and (7), iodide ($I^-$) reacts with the species to be measured to form iodine ($I_2$), the concentration of which is determined by measurement of the electric potential developed between oxidation-reduction element 34 and reference element 36. For each mole of ozone consumed according to equation (5), three moles of iodine are produced.

The reaction of iodide with chlorine, ozone, bromine, cupric ion or other species to form iodine is the basis for determination of the concentration of these species. If the concentration of one of these species is sought, the presence of other species that react with iodine ($I^-$) to form iodine ($I_2$) will introduce errors in measurement. Care must be taken to isolate the species to be measured from others in the sample stream.

Since various changes may be made in the above method without departing from the scope of the present invention, it is intended that all matter contained in the above description or shown in the accompanying drawing shall be interpreted in an illustrative and not in a limiting sense.

What is claimed is:

1. A method of monitoring the total residual chlorine in solutions, comprising the steps of:
    continuously mixing with a sample stream of the solution, a reagent stream comprising a disassociated complex of alkali metal ion and iodide ion, and an excess amount of iodide ion, said iodide ion completely reacting with all the residual chlorine to form iodine; and
    continuously measuring in the resulting mixed stream of solution and reagent, the electric potential developed between a first and second electrode, each placed in contact with the mixture, the first having a noble metal oxidation-reduction element reflecting the ratio of iodine to iodide concentration, the second having an iodide sensitive membrane reflecting the iodide concentration whereby the concentration of iodine is determined.

2. A method as defined in claim 1 wherein said noble metal oxidation-reduction element is platinum.

3. A method as defined in claim 1 wherein said alkali metal ion is potassium.

4. A method as defined in claim 1 wherein said alkali metal ion is sodium.

5. A method as defined in claim 1 further comprising the step of:
    simultaneously measuring in the sample stream, the electric potential developed between the first and second electrode, each placed in contact with the stream, the first having a noble metal oxidation-reduction element reflecting the ratio of iodine to iodide concentration, the second having an iodide sensitive membrane reflecting the iodide concentration whereby the concentration of iodine is determined in said sample stream.

6. A method of monitoring the activity of iodine in solutions, comprising the steps of:
    continuously extracting a sample stream of the solution; and
    continuously measuring in the resulting sample stream the potential difference developed between a first and second electrode, each placed in contact with the sample stream, the first having a noble metal oxidation-reduction element reflecting the ratio of iodine to iodide concentration, the second having an iodide sensitive membrane reflecting the iodide concentration, whereby the concentration of iodine is determined.

7. A method as defined in claim 6 wherein said noble metal oxidation-reduction element is platinum.

8. A method as defined in claim 6 wherein said alkali metal ion is potassium.

9. A method as defined in claim 6 wherein said alkali metal ion is sodium.

* * * * *